(12) United States Patent
Wang

(10) Patent No.: US 8,486,050 B2
(45) Date of Patent: Jul. 16, 2013

(54) BUBBLE-TYPE NOSE CLEANER

(75) Inventor: Ming Yang Wang, Nantou (TW)

(73) Assignee: Jackey Chiou, Nantou (TW)

( * ) Notice: Subject to any disclaimer, the term of this patent is extended or adjusted under 35 U.S.C. 154(b) by 500 days.

(21) Appl. No.: 12/706,703

(22) Filed: Feb. 16, 2010

(65) Prior Publication Data

US 2010/0137781 A1 Jun. 3, 2010

Related U.S. Application Data

(63) Continuation-in-part of application No. 12/231,218, filed on Aug. 29, 2008, now abandoned, which is a continuation-in-part of application No. 11/378,942, filed on Mar. 17, 2006, now abandoned.

(51) Int. Cl.
*A61M 16/14* (2006.01)
*A61M 31/00* (2006.01)

(52) U.S. Cl.
CPC ............... *A61M 16/14* (2013.01); *A61M 31/00* (2013.01)
USPC ............................................ 604/540; 604/24

(58) Field of Classification Search
USPC .................. 604/94.01, 24, 132, 313, 540
See application file for complete search history.

(56) References Cited

U.S. PATENT DOCUMENTS

| | | | |
|---|---|---|---|
| 858,996 A * | 7/1907 | Lamport | 604/94.01 |
| 1,502,163 A * | 7/1924 | Sprague | 604/36 |
| 1,533,618 A * | 4/1925 | Taylor, Jr. | 604/94.01 |
| 2,078,180 A * | 4/1937 | Kronenberg | 604/28 |
| 2,135,052 A * | 11/1938 | Rose | 604/24 |
| 2,280,992 A * | 4/1942 | Wright et al. | 604/30 |
| 2,511,973 A * | 6/1950 | De La Sierra | 604/30 |
| 3,366,061 A * | 1/1968 | Adams | 137/154 |
| 3,393,673 A * | 7/1968 | Mattingly | 601/162 |
| 3,663,117 A * | 5/1972 | Warren | 415/116 |
| 3,671,151 A * | 6/1972 | Duke | 417/411 |
| 3,762,411 A * | 10/1973 | Lloyd et al. | 604/151 |
| 3,825,374 A * | 7/1974 | Kondo | 417/413.1 |
| 4,349,131 A * | 9/1982 | Arabian | 222/135 |
| 4,403,611 A * | 9/1983 | Babbitt et al. | 604/73 |
| 4,406,591 A * | 9/1983 | Louis | 417/363 |
| 4,655,197 A * | 4/1987 | Atkinson | 601/161 |
| 4,900,316 A * | 2/1990 | Yamamoto | 604/313 |
| 4,931,000 A * | 6/1990 | Fleming, Jr. | 417/534 |
| 5,011,379 A * | 4/1991 | Hashimoto | 417/360 |
| 5,181,908 A * | 1/1993 | Bell | 604/24 |
| 5,899,878 A * | 5/1999 | Glassman | 604/48 |
| 5,989,217 A * | 11/1999 | Ohki et al. | 604/94.01 |

(Continued)

*Primary Examiner* — Melanie Hand
*Assistant Examiner* — Paula Craig
(74) *Attorney, Agent, or Firm* — Raymond Y. Chan; David and Raymond Patent Firm

(57) ABSTRACT

A bubble-type nose cleaner includes a container, an electromagnetic pump, a nose-washing tool, and at least a bubble generating valve. The container has a containing space for storing a cleaning solution. The electromagnetic pump is communicated with the container through a negative pressure channel. The nose-washing tool is communicated with the electromagnetic pump through a positive pressure channel, thereby the nose-washing tool is applied with the cleaning solution drawn by the negative pressure and then discharges the cleaning solution when the electromagnetic pump actuates. The bubble generating valve is provide at a negative pressure channel or a positive pressure channel and has an air inletting opening provided at the negative pressure channel or the positive pressure channel for communicating the exterior with the interior, wherein a cap is used to control the gas-flow rate of the bubble generating valve.

3 Claims, 16 Drawing Sheets

U.S. PATENT DOCUMENTS

| | | | | |
|---|---|---|---|---|
| 6,022,329 | A * | 2/2000 | Arnett et al. | 601/155 |
| 6,382,935 | B1 * | 5/2002 | Mikiya et al. | 417/413.1 |
| 6,520,931 | B2 * | 2/2003 | Suh | 604/73 |
| 6,715,485 | B1 * | 4/2004 | Djupesland | 128/203.15 |
| 2002/0099331 | A1 * | 7/2002 | Burchfield | 604/94.01 |
| 2002/0151836 | A1 * | 10/2002 | Burden | 604/35 |
| 2003/0109854 | A1 * | 6/2003 | Chen | 604/540 |
| 2003/0140408 | A1 * | 7/2003 | Chung | 4/443 |
| 2003/0225427 | A1 * | 12/2003 | Chen | 606/162 |
| 2005/0159760 | A1 * | 7/2005 | Ikadai et al. | 606/131 |
| 2006/0096596 | A1 * | 5/2006 | Occhialini et al. | 128/204.18 |
| 2006/0241565 | A1 * | 10/2006 | Chiou | 604/540 |
| 2008/0221507 | A1 * | 9/2008 | Hoke et al. | 604/28 |
| 2008/0319377 | A1 * | 12/2008 | Keenan | 604/24 |
| 2009/0010778 | A1 * | 1/2009 | Wang | 417/413.1 |
| 2009/0054855 | A1 * | 2/2009 | Blott et al. | 604/290 |
| 2010/0286597 | A1 * | 11/2010 | Wang | 604/35 |

* cited by examiner

BUBBLE-TYPE NOSE CLEANER

CROSS REFERENCE TO RELATED APPLICATION

This is a Continuation-In-Part application that claims the benefit of priority under 35 U.S.C. §119 to a non-provisional application having an application Ser. No. 12/231,218 and a filing date of Aug. 29, 2008.

BACKGROUND OF THE PRESENT INVENTION

1. Field of Invention

The present invention relates to nose cleaner, and more particularly to a bubble-type nose cleaner for delivering fluid with bubbles therein to clean the nasal cavity, which is different from the traditional nose cleaners that use pressurized water flow to clean the nasal cavity, herein the nose cleaner of the present invention has a higher cleaning efficiency and avoids damaging the nasal mucosa without the need of producing high pressurized water flow.

2. Description of Related Arts

Most of upper respiratory tract infections, nasosinusitis, and nasal allergies are caused by the ataxia of the cilia on the nasal mucosa. The contaminants and the bacteria drawn in through the nose can be effectively removed by the regular movement of the cilia on the nasal mucosa, thereby protecting the health of the individual.

The nasal sprayers commonly used for "ear-nose-throat" ailments department (hereinafter, "ENT ailments") and sold in the marketplace, mainly use the ultrasonic vibrations to atomize the liquid medicines into the micro particles so that the atomized medicines can rapidly and easily be breathed into the respiratory tracts and the lungs of the human bodies for a desired treatment. However, these nasal sprayers cannot essentially mend the ataxia of the cilia.

Accordingly, the conventional nose cleaner has been invented which is filled with a cleaning solution about 35° C. to 38° C., such as oscillating armsaline. When using the nose cleaner, the user has to bend his hat downward, open the mouth and breath, and then the nose cleaner is used to inject the cleaning solution into a nasal cavity of one side of the nose. The cleaning solution flows through the nasopharynx and flows out from the nasal cavity through the other side of the nose, thereby the cleaning assists the movement of the cilia on the nasal mucosa. That is helpful in the prevention of colds, allergic rhinitis, nasosinusitis, halitosis, backflow of the snot, and etc.

Currently, the technology of the nose cleaner s still focuses on the control of the intensity of the water flow. Although the water flow with a high pressure will provide better cleaning, it may cause damage to the nasal mucosa even resulting in nose bleeding. If the pressure of the water flow is too low, the effect of the cleaning will be reduced. As the proper intensity of the water flow varies from person to person, it is hard for the producers to handle. Hence, the inventor of the present invention actively sought for a solution and finally invented a bubble-type nose cleaner providing a water flow as further disclosed in the present invention in order to overcome the technical defects of the conventional nose cleaner that the water flow is difficult to control.

SUMMARY OF THE PRESENT INVENTION

The present invention provides a nose cleaner, which comprises:

a fluid container having a containing space for storing a cleaning solution therein;

a pressure fluid channel comprising a positive pressure channel and a negative pressure channel;

an electromagnetic pump communicated with the container through the negative pressure channel;

a nose-washing tool communicated with the electromagnetic pump through the positive pressure channel which comprises a spray nozzle for discharging the fluid of the cleaning solution drawn from the container by the negative pressure produced by the electromagnetic pump; and a bubble generating valve provided at the pressure fluid channel, wherein the bubble generating valve draws gas outside, such as air, into the cleaning solution due to the negative pressure of the fluid. Further, the bubbled fluid is discharged from the spray nozzle with gas bubbles therein, thereby allowing the nose cleaner to use the oscillating force of the bubbles to assist the movement of the cilia on the nasal mucosa instead of using the conventional strongly pressurized water flow. Hence, the bubble-type nose cleaner has a higher cleaning efficiency and avoids damaging the nasal mucosa.)

These and other objectives, features, and advantages of the present invention will become apparent from the following detailed description, the accompanying drawings, and the appended claims.

DETAILED DESCRIPTION OF THE PREFERRED EMBODIMENT

Referring to FIGS. 1 to 6, a bubble-type nose cleaner according to a preferred embodiment of the present invention is illustrated, which comprises the following elements.

Figure 1:
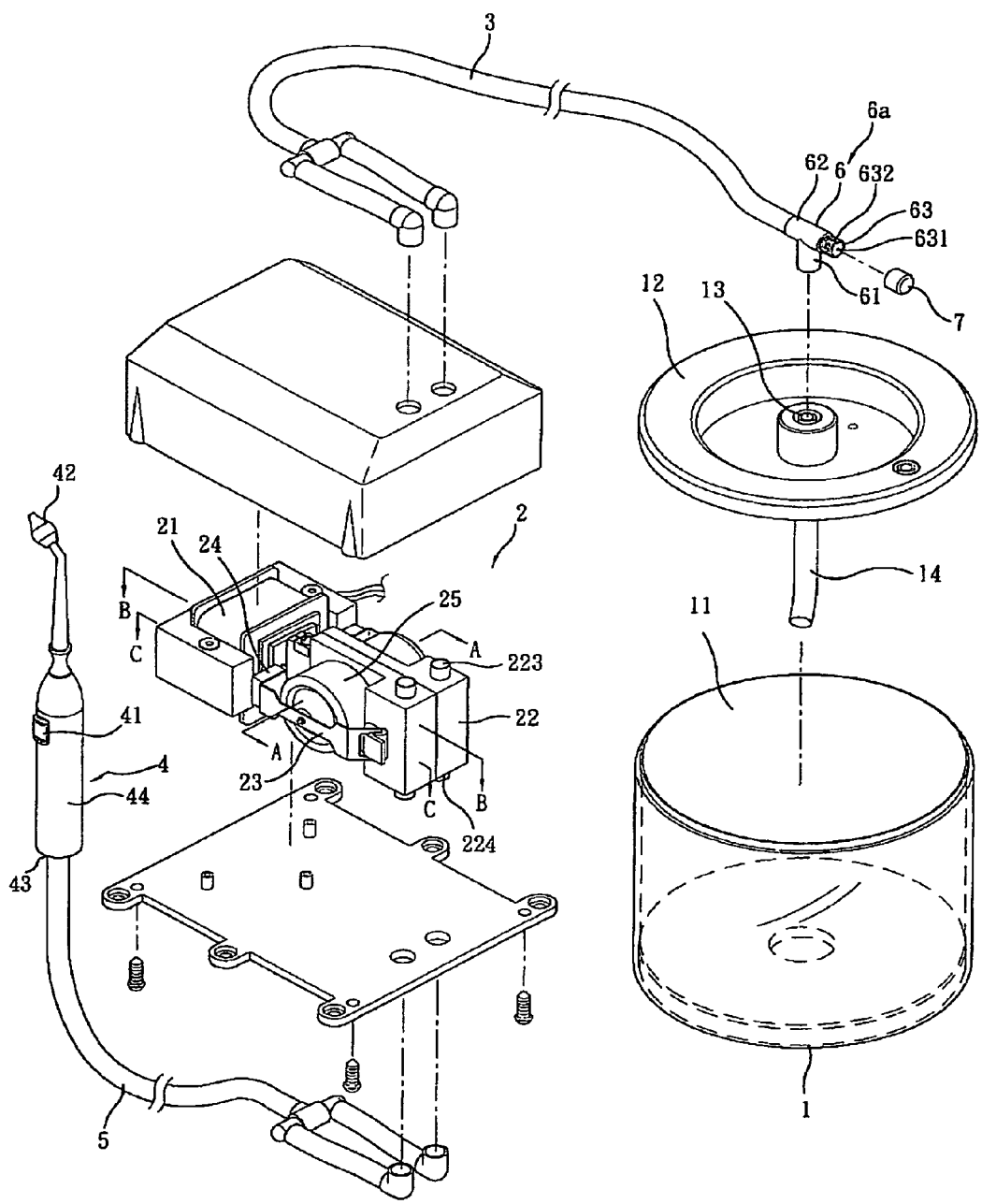
FIG. 1 is an exploded perspective view of a bubble-type nose cleaner according to a preferred embodiment of the present invention.

A fluid container 1, as shown in FIG. 1, has a containing space 11 therein for storing a cleaning solution and an upper opening enabling an upper cover 12 to cover thereon. The upper cover 12 has a connecting member 13 provided thereon for communicating the containing space 11 with outside. A suction member 14 made of soft material is connected to a bottom of the connecting member 13 for providing the cleaning solution stored in the containing space 11 of the container 1 as a fluid source according to the present invention. 1

An electromagnetic pump 2, as shown in FIG. 1, FIG. 5A, FIG. 5B, FIG. 5C and FIG. 5D, comprises an electromagnetic member 21 and a pair of valve housing confronting hollow valve housings 22 which divided into an upper chamber 225 and a lower chamber 226. Each of the two outer opposing sides of the pair of hollow valve housings provides an oscillating arm 23, wherein magnetic members 24 are provided at movable ends of the oscillating arms 23 respectively and rubber made elastic hats 25 are sealedly mounted between the hollow valve housings 22 and the oscillating arms 23 respectively so that valve housing the electromagnetic member 21 substantially actuates the magnetic members 24 to drive the two oscillating arms 23 to control the expanding and compressing of the hats 25.

Each of the two valve housings 22 further comprises a check valve 221 and a second reverse check valve 222 disposed within the respective hat 25, and an inlet aperture 223 and an outlet aperture 224 provided thereon, wherein the inlet apertures 223 are communicated with the suction member 14 of the container 1 and the respectively upper chamber 225 through the negative pressure channel 3 and the outlet aperture 224 is communicated with a nose-washing tool 4 and the lower chamber 226 through the positive pressure channel 5. Accordingly, the check valve 221 can be opened and the reverse check valve 222 can be closed during the expanding of the respective hat 25 in order to draw the cleaning solution in the container 1 into the hat 25 through the upper chamber 225 due to the negative pressure at the respective inlet aperture 223. Also, the reverse check valve 222 can be opened and the check valve 221 can be closed during the compressing of the respective hat 25 so as to delivering the positively pressured cleaning solution within the respective hat 25 to the respective outlet aperture 224 through the lower chamber 226. The electromagnetic pump 2 is embodied to be received in a case 26 and the inlet aperture 223 and the outlet aperture 223 are extended through the outer wall of the case 26 to communicate with the negative pressure channel 3 and the positive pressure channel 5 respectively.

A nose-washing tool 4 comprises a handle 44 which has a fluid inlet 43 at one end and a spray nozzle 42 at the other end for discharging fluid, and a switch 41 disposed between the two ends for switching on and off the fluid flow, wherein the fluid inlet 43 is communicated with the outlet aperture (224) of the electromagnetic pump 2 through the negative pressure channel 3, thereby when the electromagnetic pump 2 is activated, the cleaning solution in the container 1 can be drawn through the negative pressure channel 3 to discharge from the spray nozzle 42 of the nose-washing tool 4.

Figure 4A:
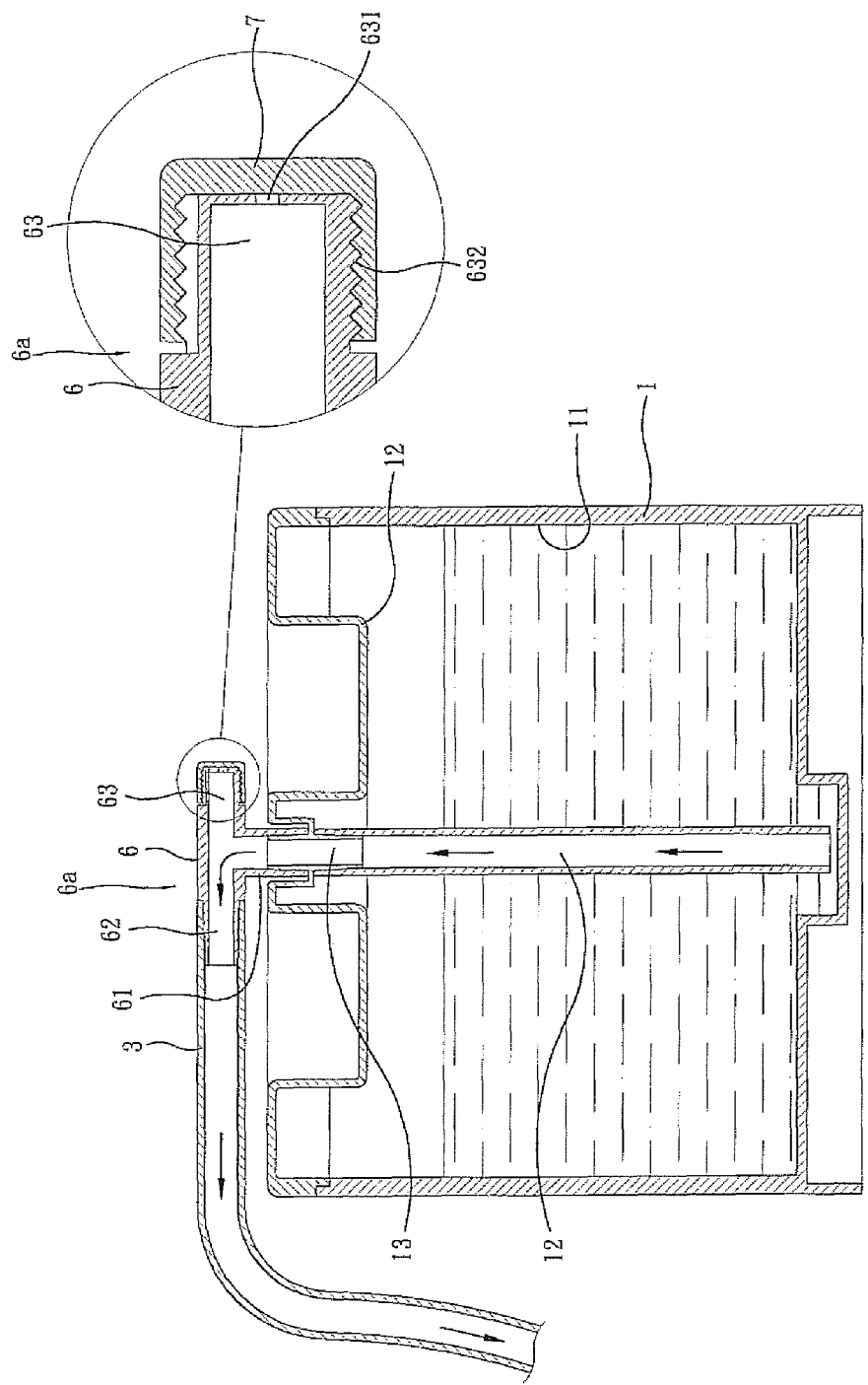
FIG. 4A is a sectional view illustrating the structure of the bubble generating valve in closed condition of the bubble-type nose cleaner according to the above preferred embodiment of the present invention.
Figure 4B:
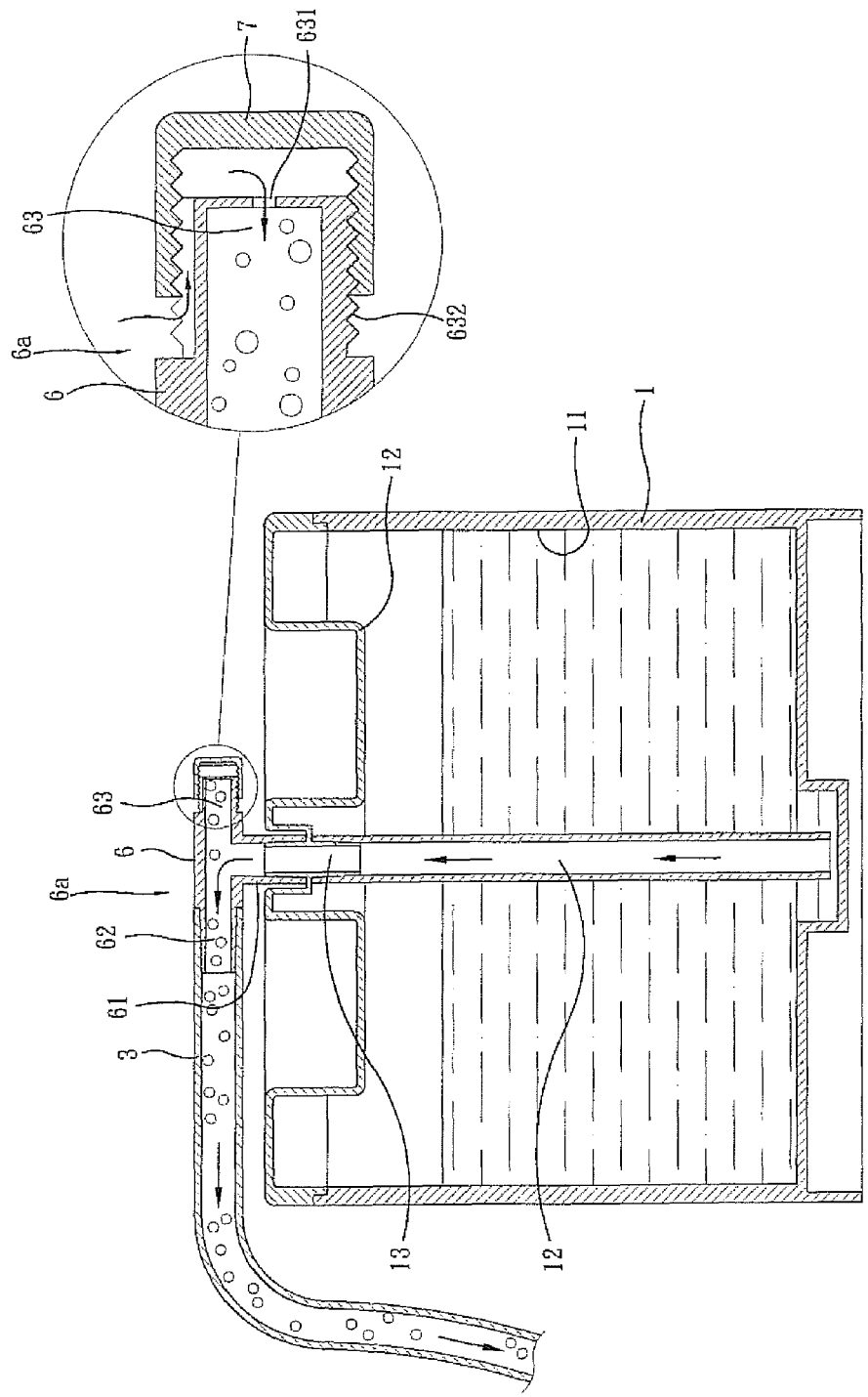
FIG. 4B is a sectional view illustrating the structure of the bubble generating valve in opened condition of the bubble-type nose cleaner according to the above preferred embodiment of the present invention.
Figure 5A:
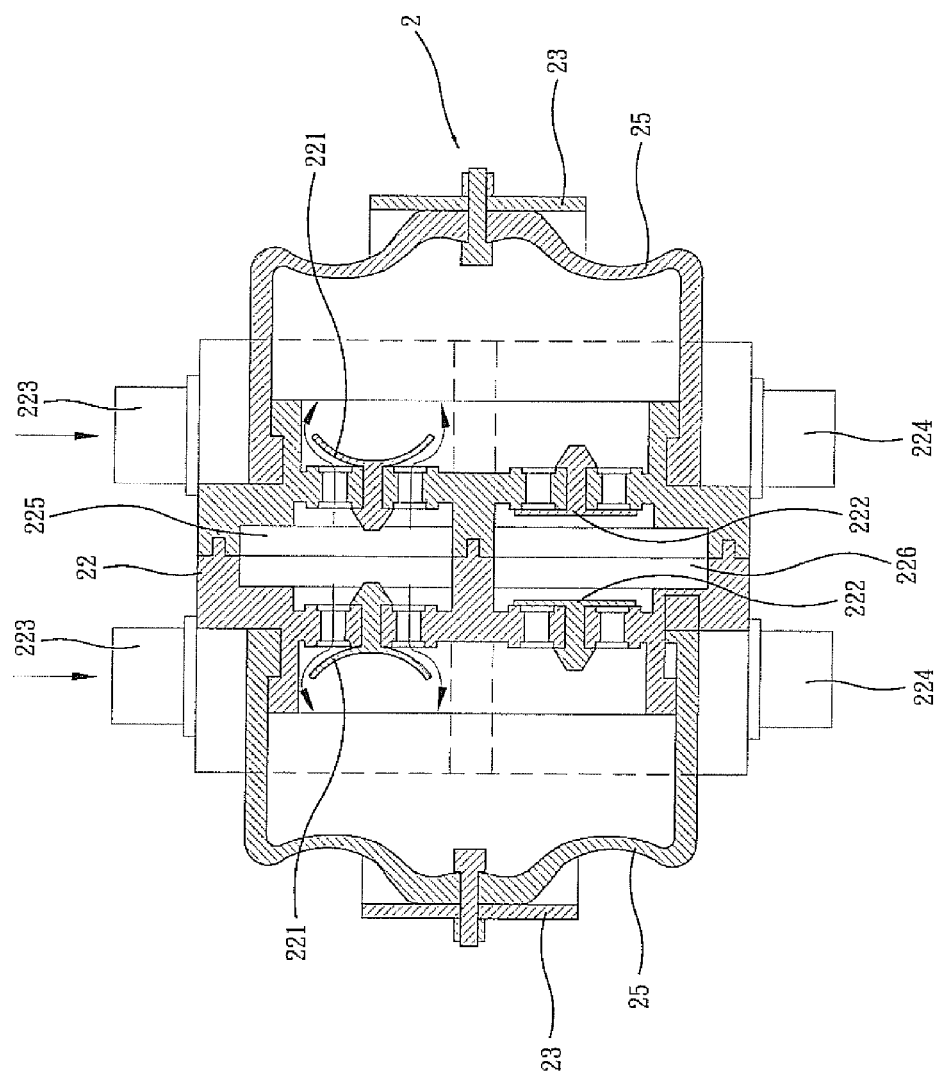
FIG. 5A is an A-A sectional view of the drawn electromagnetic pump of the bubble-type nose cleaner according to the above preferred embodiment of the present invention.
Figure 5B:
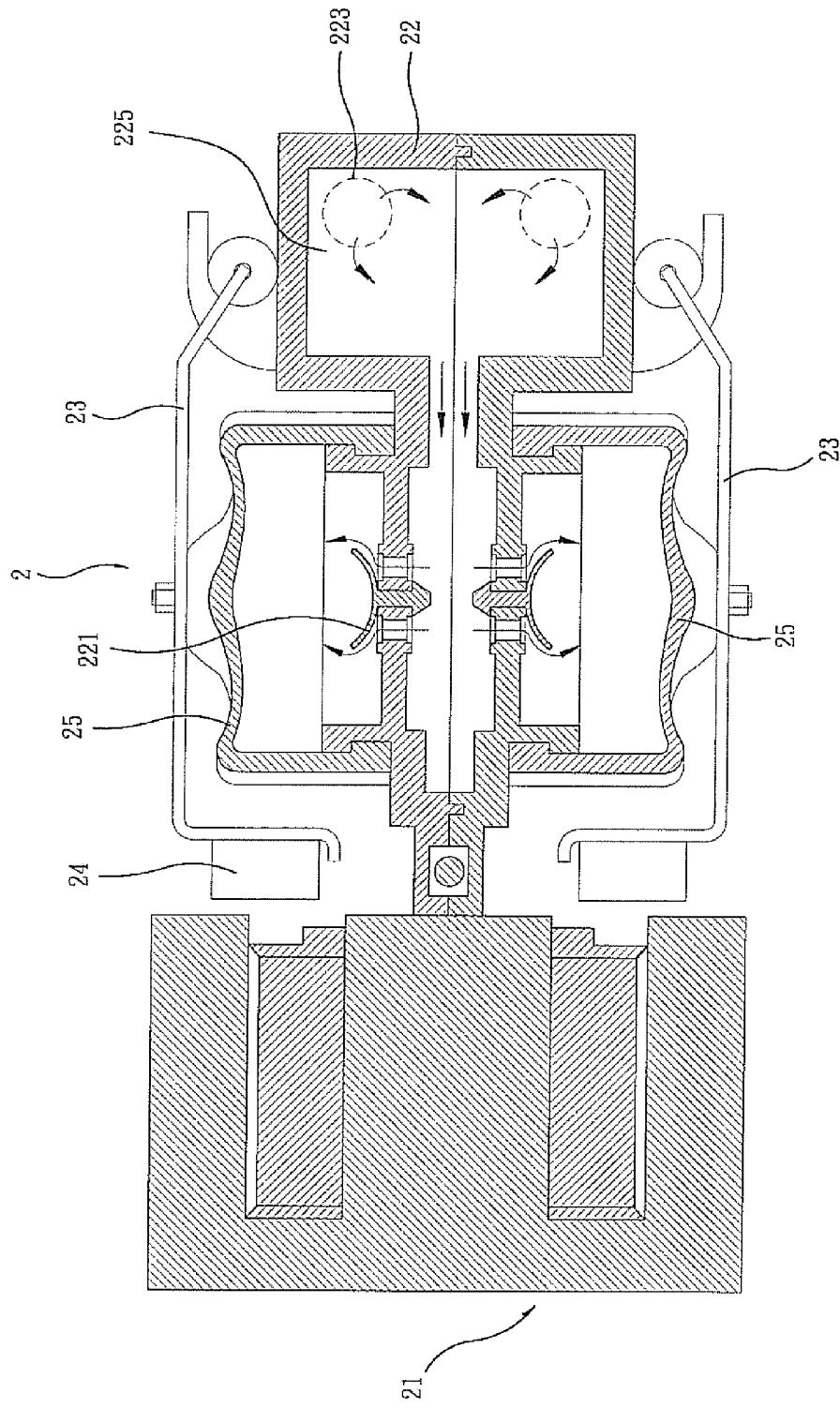
FIG. 5B is a B-B sectional view of the drawn electromagnetic pump of the bubble-type nose cleaner according to the above preferred embodiment of the present invention.
Figure 5C:
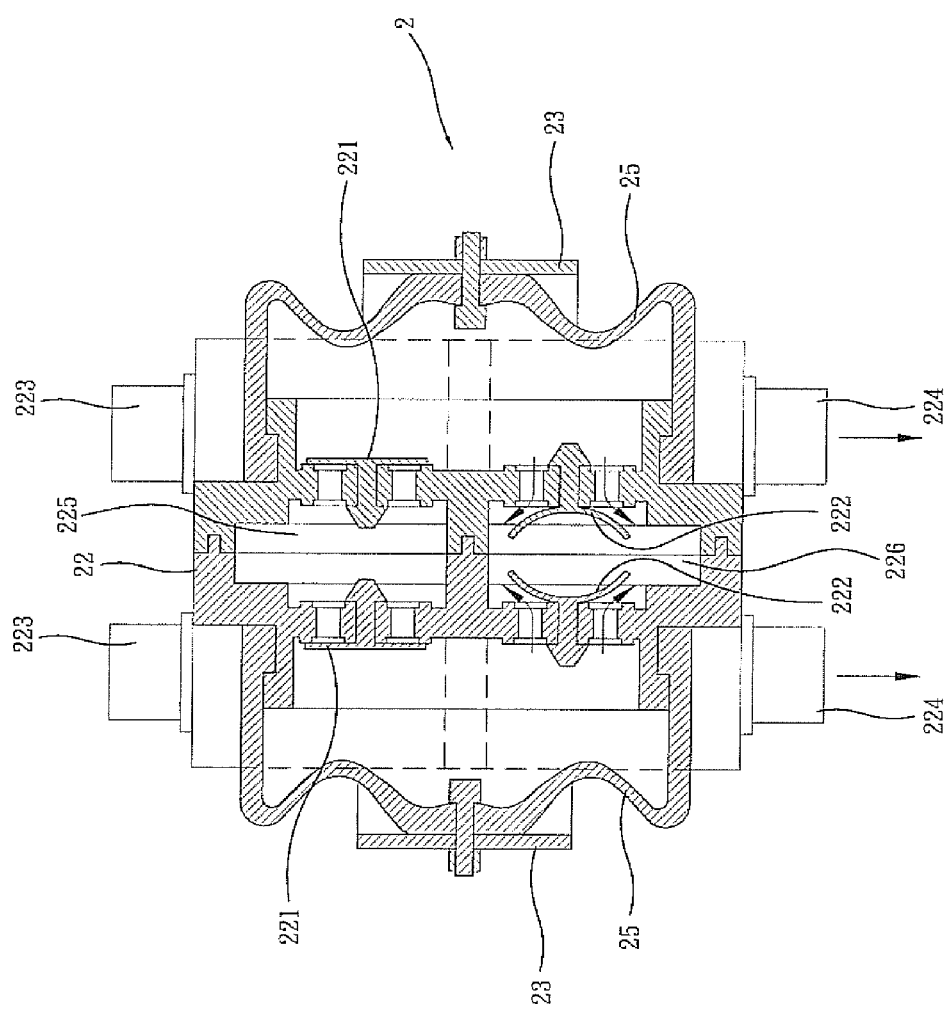
FIG. 5C is an A-A sectional view of the compressed electromagnetic pump of the bubble-type nose cleaner according to the above preferred embodiment of the present invention.
Figure 5D:
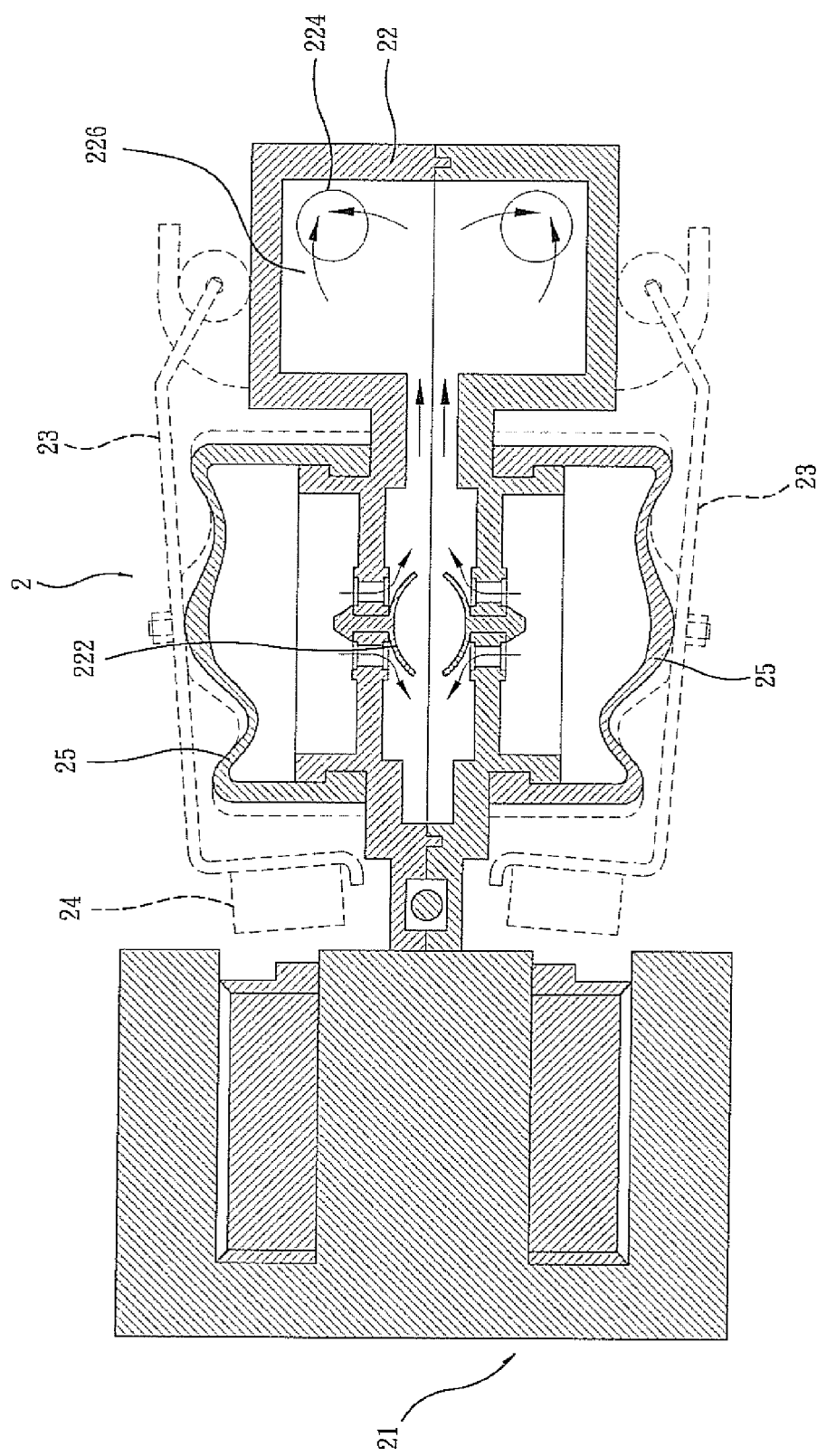
FIG. 5D is a C-C sectional view of the compressed electromagnetic pump of the bubble-type nose cleaner according to the above preferred embodiment of the present invention.
Figure 6:
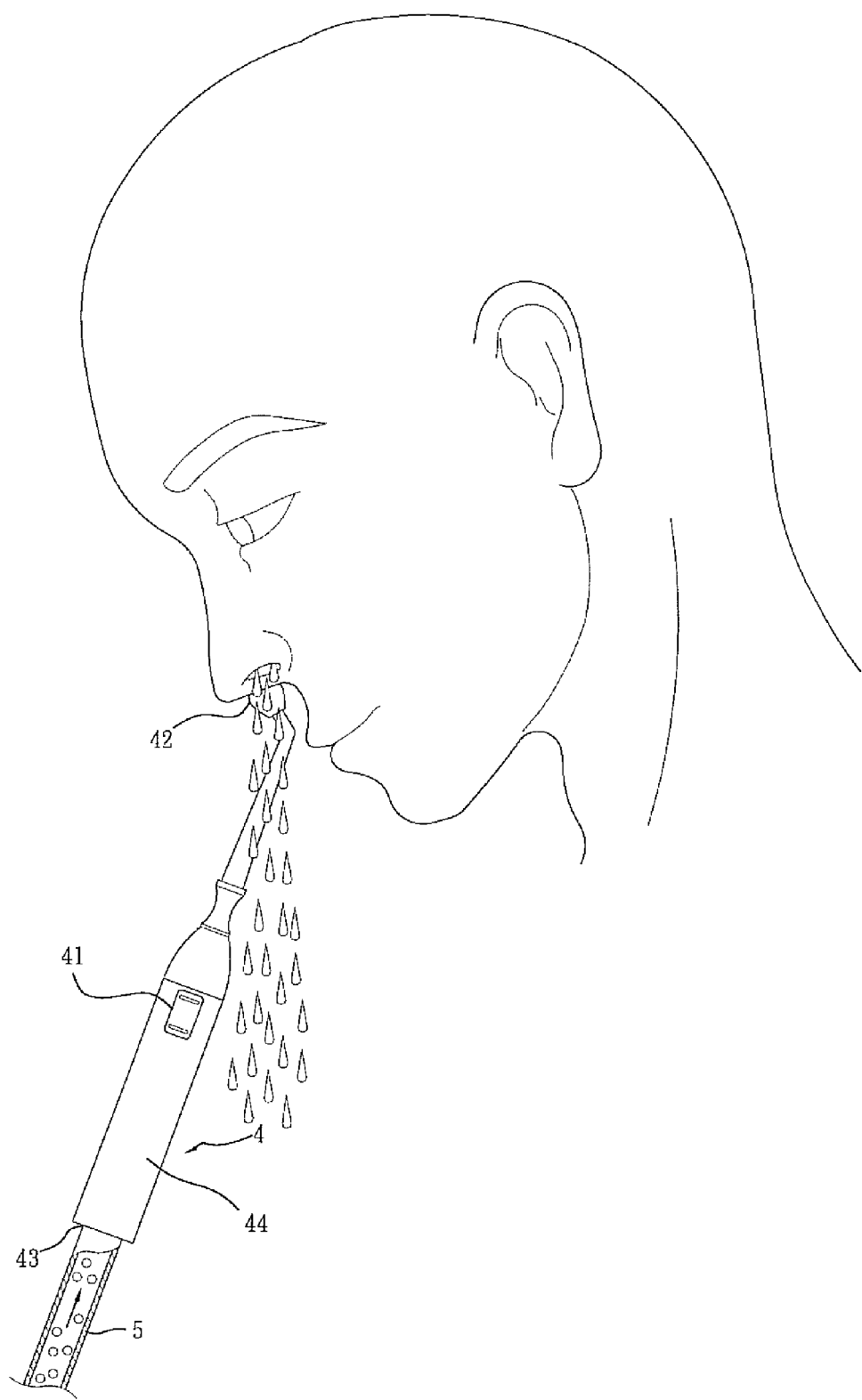
FIG. 6 is an illustration view of the use of the bubble-type nose cleaner according to above preferred embodiment of the present invention.

A bubble generating valve 6a, as shown in FIG. 4A and FIG. 4B, which is installed at the negative pressure channel 3, comprises a T-shaped three-way connecter 6 and a cap 7. The connecter 6 comprises a first tube 61 vertically extended and second and third tubes 62,63 horizontally extended, wherein the first tube 61 is communicated with the connecting member 13 of the container 1, and the second tube 62 is communicated with the negative pressure channel 3 to allow the negative pressure channel 3 to draw the cleaning solution into the container 1 through the connecter 6 and the suction member 14, and the third tube 63 has a threaded portion 632 for screwing with the cap 7, to control the gas-flow rate of an air inletting opening 631 thereof as well as the opening or closing of this inletting opening 631, so that when the electromagnetic pump 2 draws the cleaning solution into the container 1, outside air is drawn and sucked in through the air inletting opening 631 to mix with the flowing cleaning solution due to the negative pressure effect thereof and thus the cleaning solution discharged from the spray nozzle 42 substantially contains a large amount of air bubbles.

According to the present invention, as the discharged fluid contains a plurality of bubbles, the bubbles can generally contact with the nasal mucosa, so that when the bubbles in the discharged fluid break, oscillating force is generated and applied to the nasal mucosa to massage the mucocilia of the nasal mucosa and clean the dirt in the nasal cavity as well, thereby the cilia on the nasal mucosa can recover their regular movement without the need of using strong pressurized fluid. The present invention is adapted to be used by different people with different health conditions while maintaining high cleaning efficiency and avoiding damaging the nasal mucosa.

Figure 2:
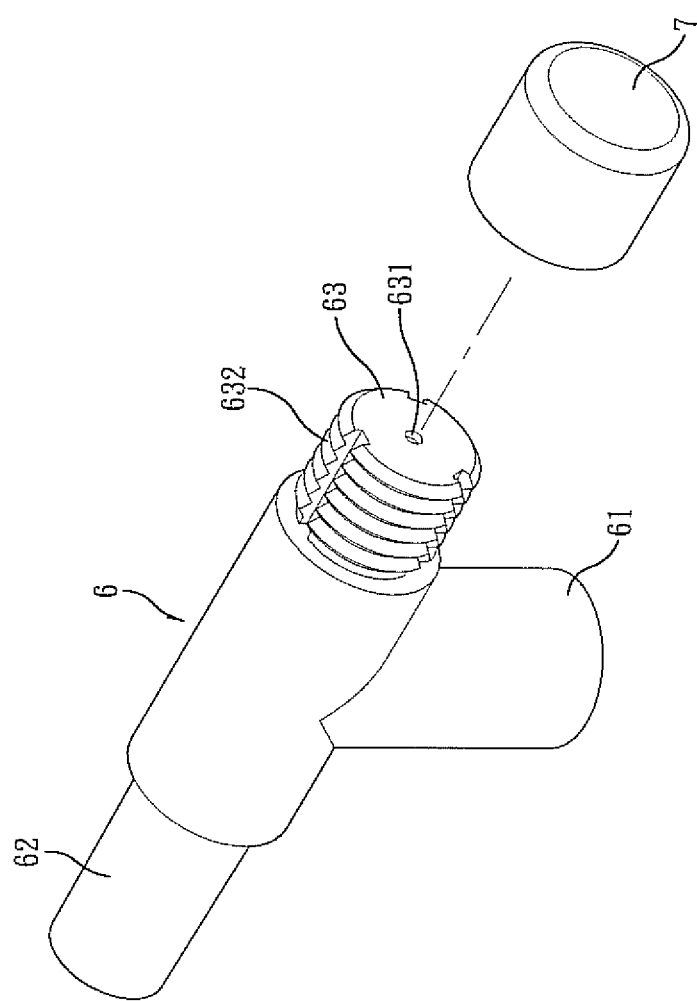
FIG. 2 is an exploded perspective view of a bubble generating valve of the bubble-type nose cleaner according to the above preferred embodiment of the present invention.
Figure 3:
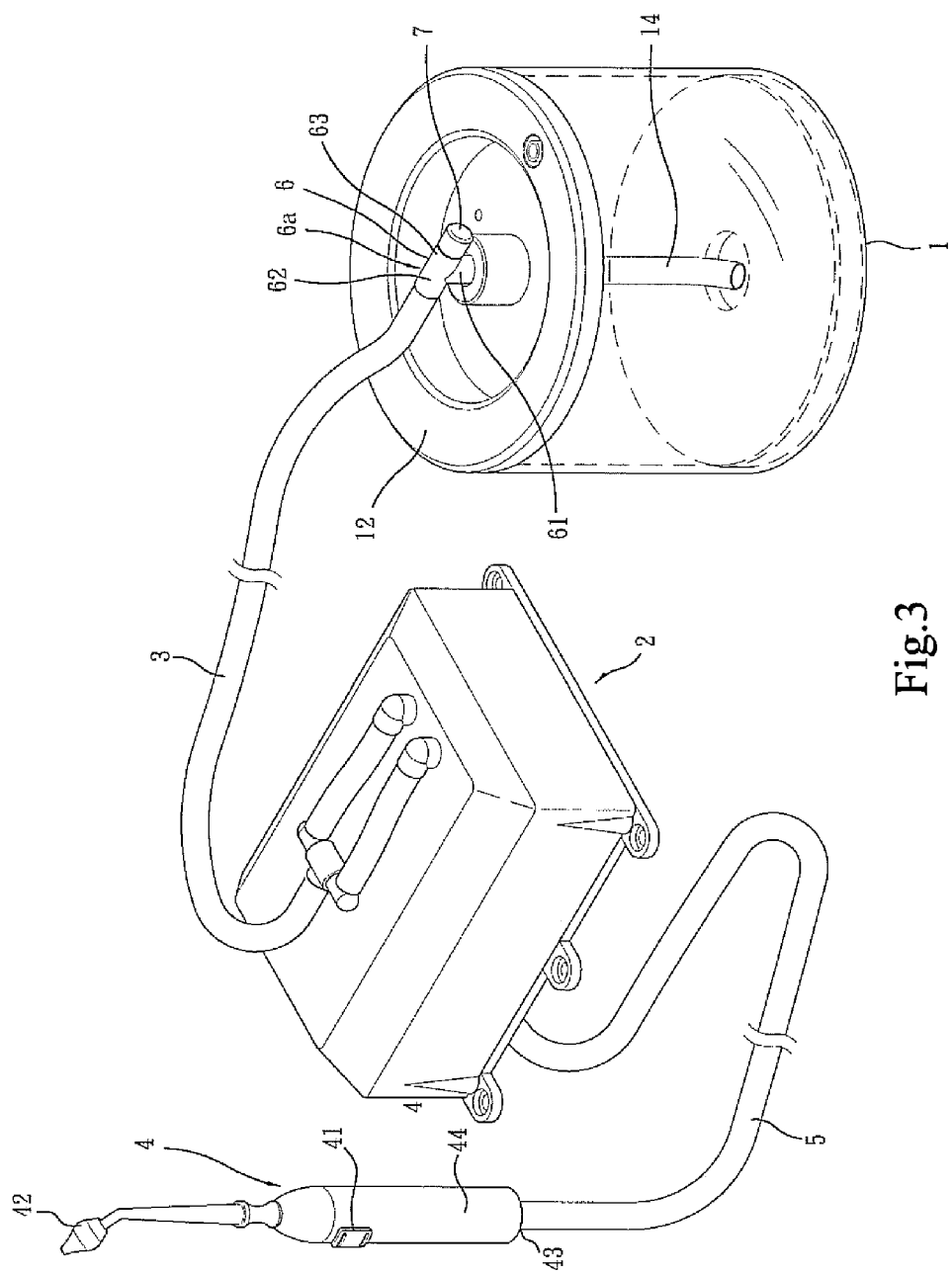
FIG. 3 is a perspective view illustrating the appearance of the bubble-type nose cleaner according to the above preferred embodiment of the present invention.
Figure 7:
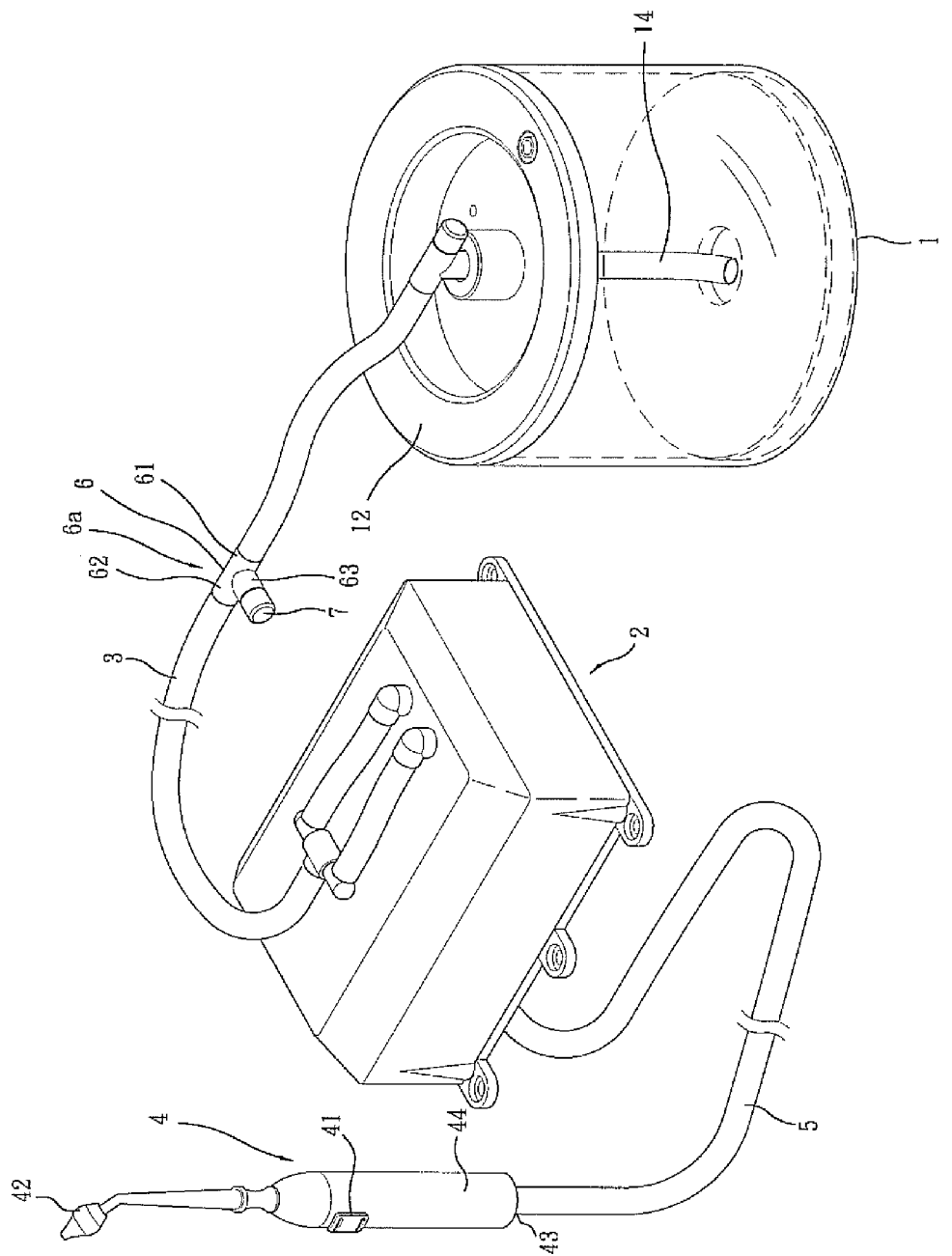
FIG. 7 is a perspective view of a bubble-type nose cleaner according to a first alternative mode of the above preferred embodiment of the present invention.

FIG. 7 further illustrates an alternative mode that the bubble generating valve 6a of the present invention is provided at the negative pressure channel 3. The bubble generating valve 6a also comprises the three-way connecter 6 and the cap 7, wherein the connecter 6 also comprises a horizontal first tube 61, a horizontal second tube 62 and a vertical third tube 63. The first tube 61 and the second tube 62 are arranged in line and are inserted into the negative pressure channel 3 in series. The third tube 63 also has an air inletting opening 631 as illustrated in FIG. 2 at an end of the third tube 63. The cap 7 is screwed to the end of the third tube 63 to control the gas-flow rate of the bubble generating valve 6a. As a result, due to the negative pressure effect of the fluid flow, the bubble generating valve 6a draws and sucks air outside into the cleaning solution flowing in the negative pressure channel 3, enabling the fluid discharged from the spray nozzle 42 containing a predetermined amount of bubbles.

Figure 8:
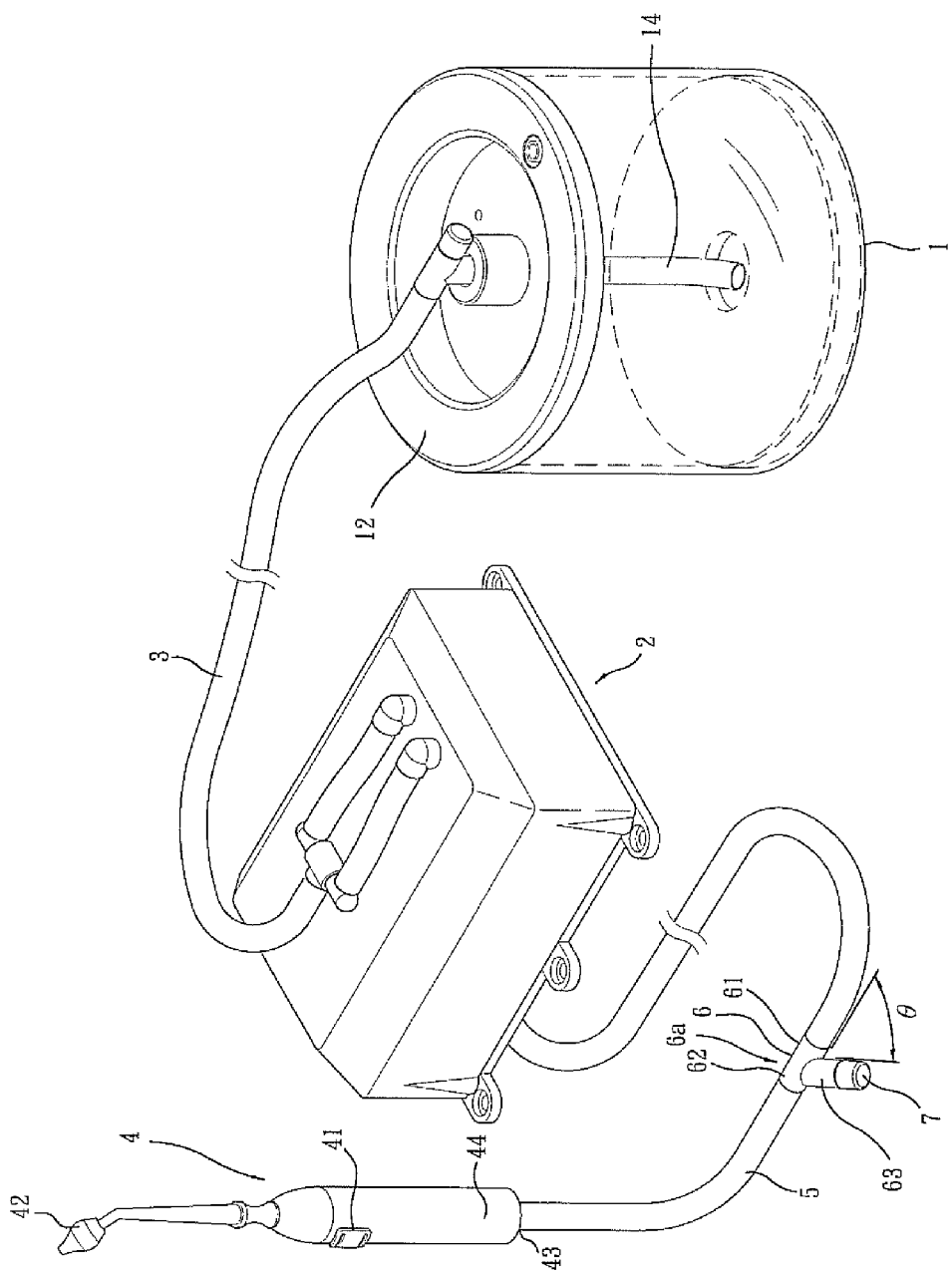
FIG. 8 is a perspective view of a bubble-type nose cleaner according to a second alternative mode of the above preferred embodiment of the present invention.

FIG. 8 illustrates another alternative mode that the bubble generating valve 6a of the present invention can also be provided at the positive pressure channel 5. The bubble generating valve 6a also comprises a three-way connecter 6 and the cap 7, wherein the connecter 6 also comprises a horizontal first tube 61, a horizontal second tube 62 and a third tube 63, wherein the intersection angle θ between the first tube 61 and the third tube 63 is less than 90°. The first tube 61 is communicated with the positive pressure channel 5 to allow the fluid to flow into the positive pressure channel 5. The second tube 62 is communicated with the positive pressure channel 5 to allow the fluid to drain out of the positive pressure channel 5. The third tube 63 also has an air inletting opening 631 as illustrated in FIG. 2 at the end of the third tube 63. The cap 7 is screwed to the third tube 63 to control the gas-flow rate of the bubble generating valve 6a. As a result, due to the negative pressure effect of the fluid flow, the bubble generating valve 6a draws and sucks air outside into the cleaning solution flowing in the positive pressure channel 5, enabling the fluid discharged from the spray nozzle 42 containing a predetermined amount of bubbles. The structures and the functions of the bubble generating valve 6a are equivalent to that in FIG. 7.

Figure 9:
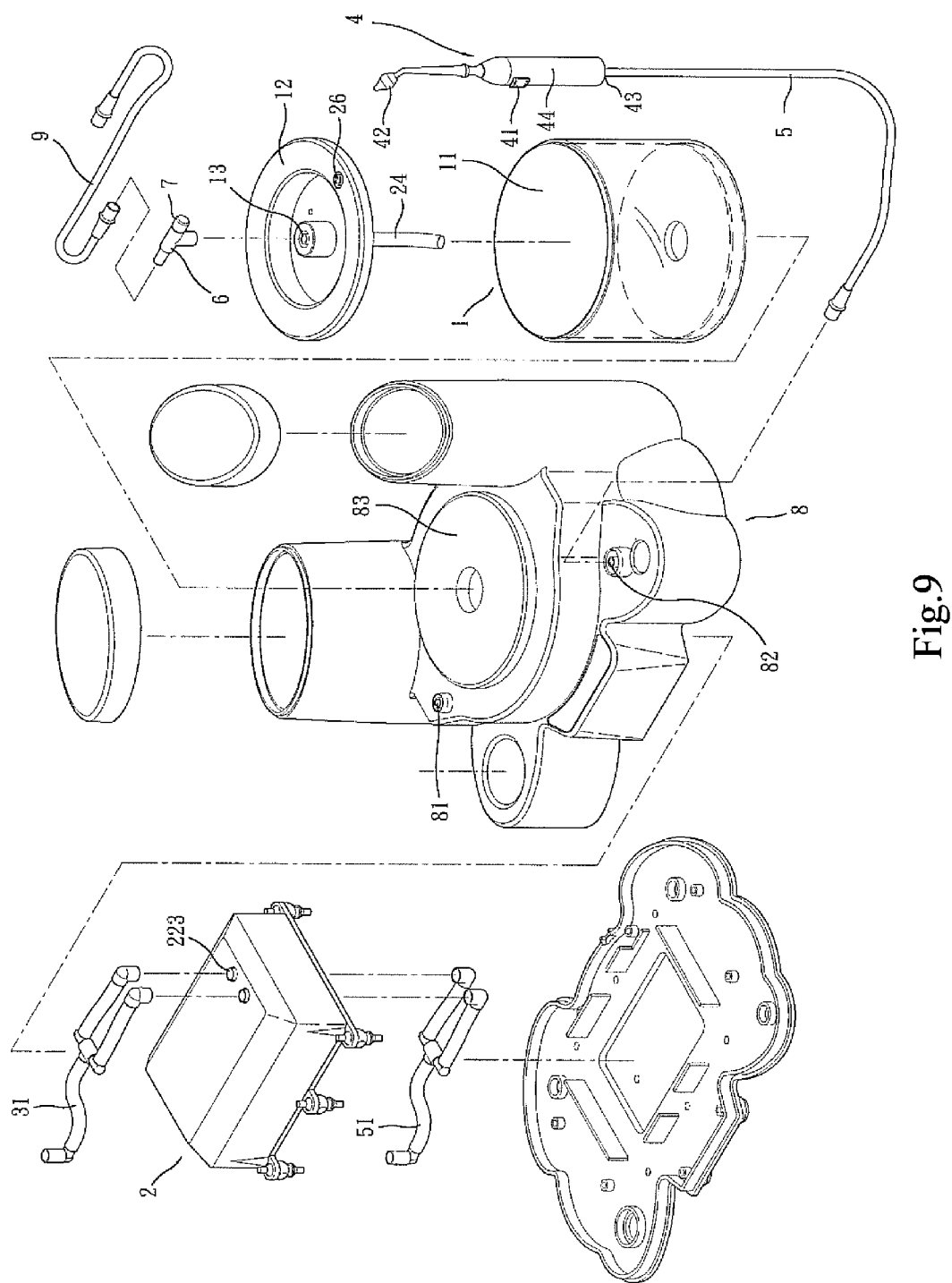
FIG. 9 is an exploded perspective view of a bubble-type nose cleaner according to a third alternative mode of the above preferred embodiment of the present invention.
Figure 10:
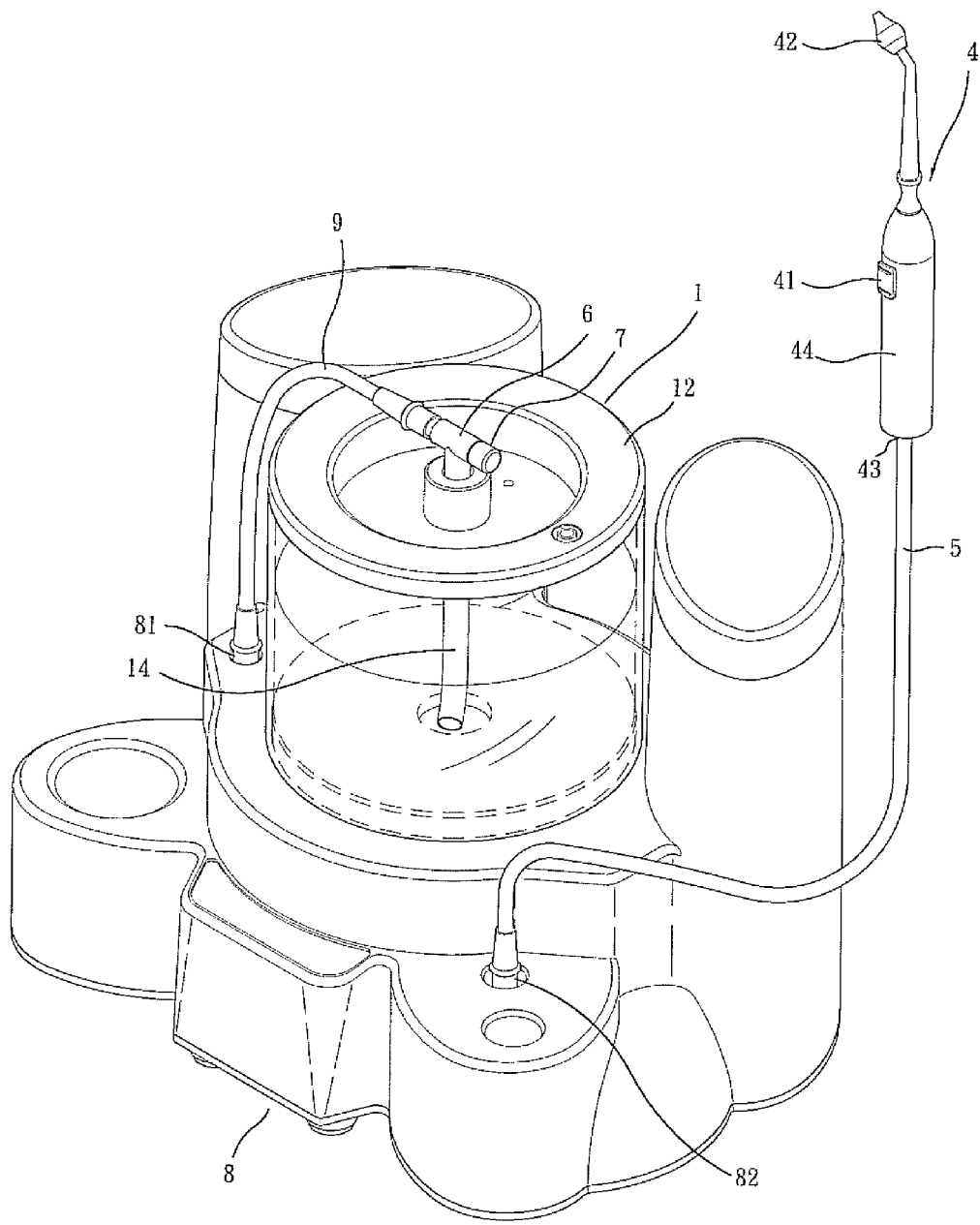
FIG. 10 is a perspective view of the bubble-type nose cleaner according to the above third alternative mode of the above preferred embodiment of the present invention.
Figure 11:
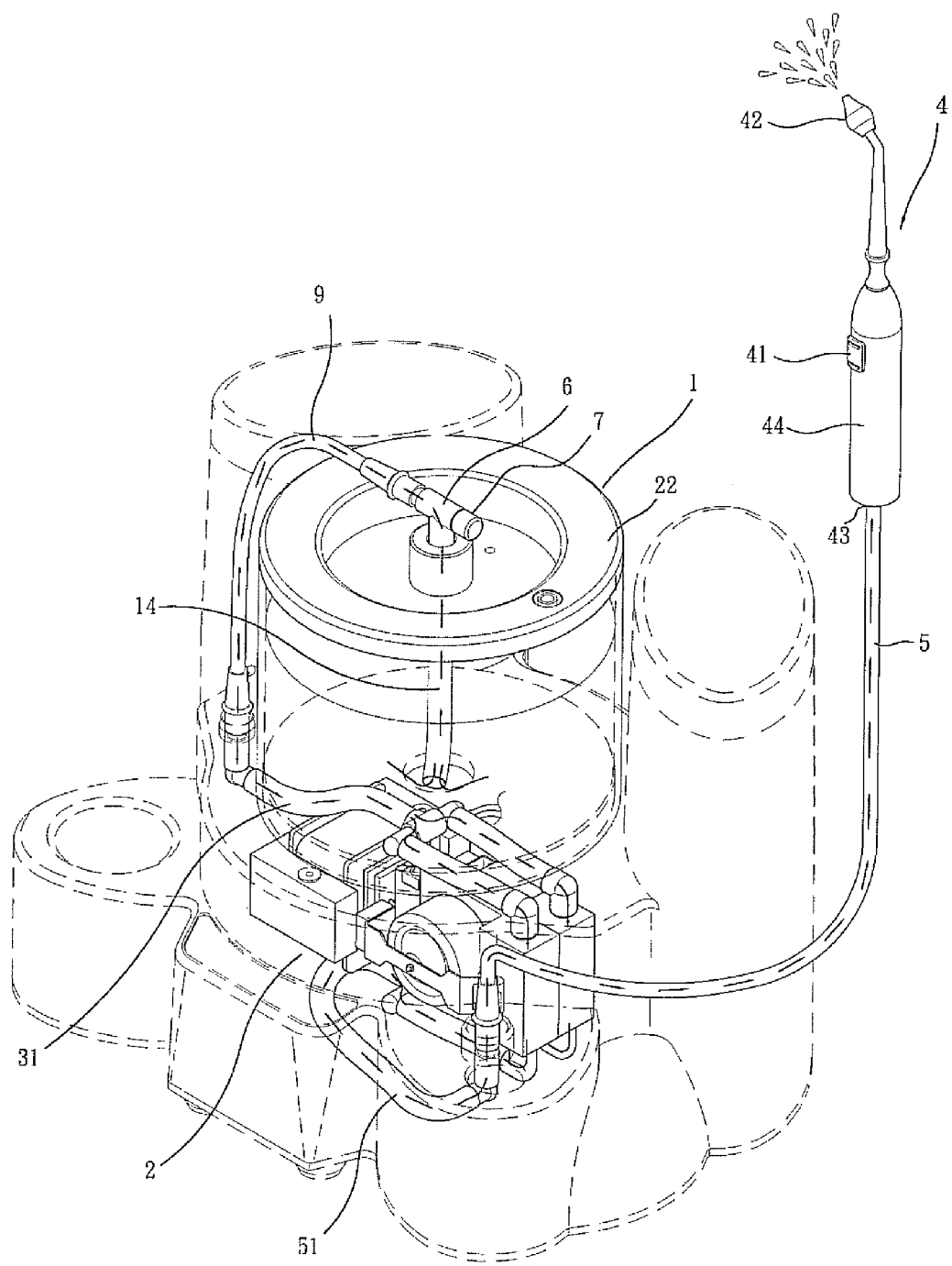
FIG. 11 illustrates the direction of the fluid flow in FIG. 10.

As shown in FIGS. 9 to 11, the electromagnetic pump 2 of the present invention is received in a body 8, which comprises a platform 83 provided thereon for the container 1 mounting on the platform 83. The body 8 further comprises a negative pressure joint 81 and a positive pressure joint 82, wherein the negative pressure joint 81 is communicated with the inlet aperture 223 of the electromagnetic pump 2 through a negative pressure channel 31 and the positive pressure joint 82 is communicated with the outlet aperture 224 of the electromagnetic pump 2 through a positive pressure channel 51. The nose-washing tool 4 is communicated with the positive pressure joint 82 through the positive pressure channel 5, and the negative pressure joint 81 is communicated with the container 1 through a pipe 9. As a result, when the electromagnetic pump 2 works, the negative pressure channel 31 draws and sucks the cleaning solution into the container 1, wherein the cleaning solution is a saline about 35° C. to 38° C. generally. Accordingly, the cleaning solution is injected by the nose-washing tool 4 into one side of the nose to flow out through another side of the nose through the nasopharynx to remove dirt in the nasal cavity and thereby the cilia on the nasal mucosa can recover their regular movement. The presence of the body 8 renders the bubble-type nose cleaner of the present invention having a more beautiful appearance.

Figure 12:
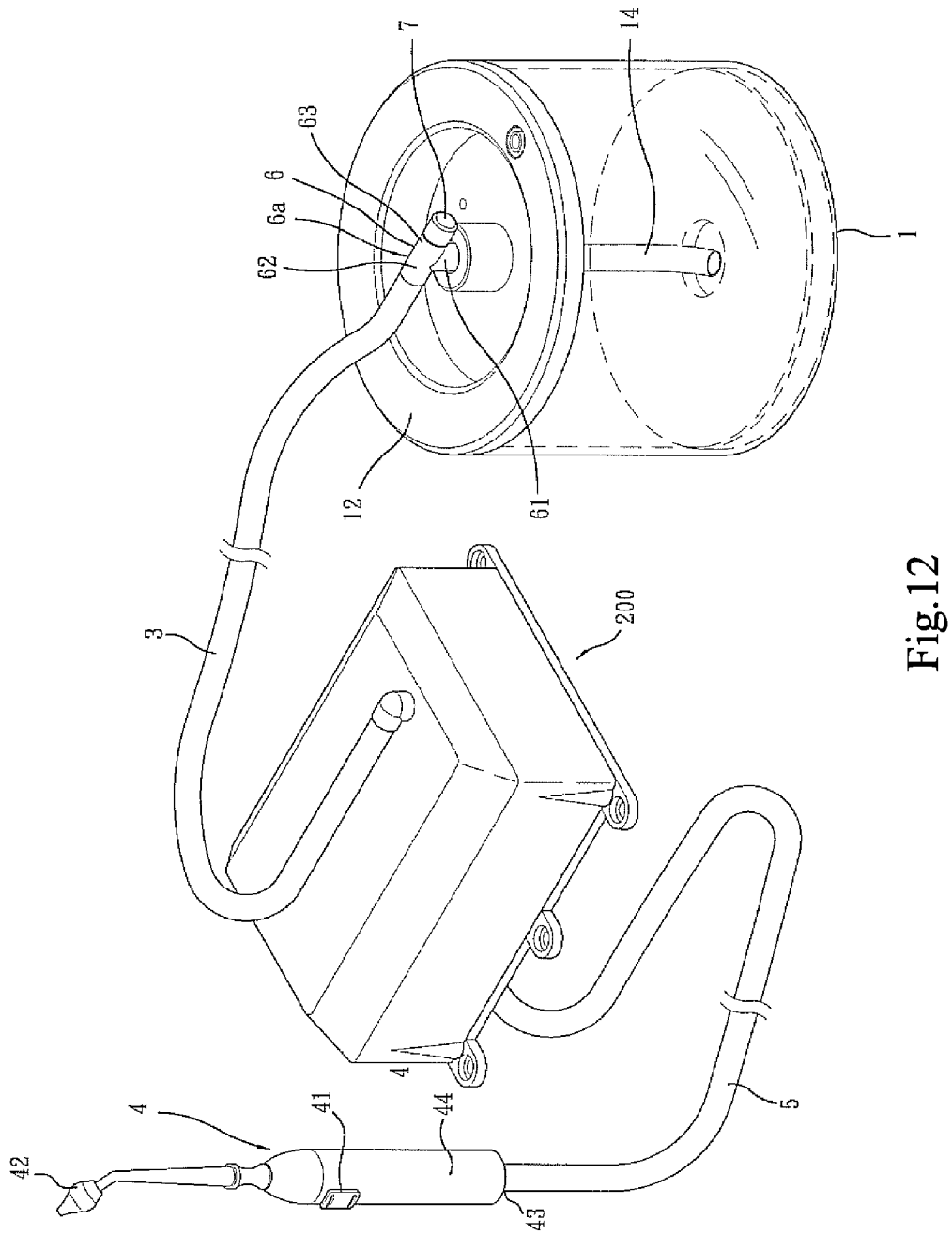
FIG. 12 is a perspective view of a bubble-type nose cleaner according to a fifth alternative mode of the above preferred embodiment of the present invention.

The electromagnetic pump 2 is a good choice to be used as the power source for drawing the cleaning solution into the container 1. This does not mean the present invention can only adopt the electromagnetic pump 2 as the device used for drawing the cleaning solution into the container 1. According to FIG. 12, other power sources can be used instead of the pump 200 for drawing the cleaning solution into the container 1, such as motor and the like for drawing water.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A bubble-type nose cleaner, which comprises:
a container having a containing space for storing a cleaning solution;
a pump communicated with said container through a negative pressure channel;
a nose-washing tool communicated with said pump through a positive pressure channel, which comprises a spray nozzle for discharging said cleaning solution drawn from said container by said negative pressure channel when said pump is activated; and
a bubble generating valve, which draws and sucks gas outside into said cleaning solution due to a negative pressure of said cleaning solution, whereby said cleaning solution discharged from said nose-washing tool contains bubbles therein,
wherein said pump is an electromagnetic pump, which further comprises an electromagnetic member and at least a valve housing, wherein said valve housing comprises an oscillating arm provided at an outer side thereof, a magnetic member provided at a moveable end of said oscillating arm, and a hat sealedly mounted between said valve housing and said oscillating arm, wherein said electromagnetic member actuates said magnetic member to drive said oscillating arm to control an expanding and a compressing of said hat, wherein said valve housing further comprises a check valve and a reverse check valve disposed in said hat, and has an inlet aperture and an outlet aperture provided thereon, wherein said inlet aperture is communicated with said container through said negative pressure channel and said outlet aperture is communicated with said spray nozzle through said positive pressure channel, wherein when said hat is arranged to expand to open said check valve and to close said reverse check valve, said cleaning solution is allowed to be drawn at said inlet aperture and to flow through from said container to said hat, wherein when said hat is arranged to compress to open said reverse check valve and to close said check valve, said cleaning solution is allowed to flow through from said hat and to be discharged at said outlet aperture.

2. The bubble-type nose cleaner, as recited in claim 1, wherein said nose-washing tool has a handle with a fluid inlet at one end and a spray nozzle at the other end for discharging fluid, wherein a switch is disposed between said two ends for switching on and off said fluid flow, wherein said fluid inlet is communicated with said pump through said negative pressure channel.

3. A bubble-type nose cleaner, which comprises:
a container having a containing space for storing a cleaning solution;
a pump communicated with said container through a negative pressure channel;
a nose-washing tool communicated with said pump through a positive pressure channel, which comprises a spray nozzle for discharging said cleaning solution drawn from said container by said negative pressure channel when said pump is activated; and
a bubble generating valve, which draws and sucks gas outside into said cleaning solution due to a negative pressure of said cleaning solution, whereby said cleaning solution discharged from said nose-washing tool contains bubbles therein, wherein said pump is received in a body, which comprises a platform provided thereon for said container mounting thereon, wherein said body further comprises a negative pressure joint communicated with said pump through a negative pressure channel and a positive pressure joint communicated with said pump through said positive pressure channel, wherein said nose-washing tool is communicated with said positive pressure joint through said positive pressure channel, and said negative pressure joint is communicated with said container through a pipe,
wherein when said pump is actuated, said negative pressure channels draws and sucks said cleaning solution in said container and said nose-washing tool discharges said cleaning solution, wherein said pump is an electromagnetic pump, which further comprises an electromagnetic member and at least a valve housing, wherein said valve housing has an oscillating arm provided at an outer side thereof, and a plurality of magnetic members provided at a moveable end of said oscillating arm, and a hat is sealedly mounted between said valve housing and said oscillating arm, wherein said electromagnetic pump actuates said magnetic member to drive said oscillating arm to control an expanding and a compressing of said hat, wherein said valve housing further has a check valve and a reverse check valve disposed in said hat, and has an inlet aperture and an outlet aperture provided thereon, wherein said inlet aperture is communicated with said container through said negative pressure channel and said outlet opening is communicated with said spray nozzle through said positive pressure channel.

* * * * *